United States Patent [19]

Lewis et al.

[11] Patent Number: 4,864,044

[45] Date of Patent: Sep. 5, 1989

[54] TIN CONTAINING ACTIVATED SILICON FOR THE DIRECT REACTION

[75] Inventors: Kenrick M. Lewis, New York, N.Y.; Thomas E. Childress, Washington, Ohio

[73] Assignee: Union Carbide Corporation, Danbury, Conn.

[21] Appl. No.: 702,230

[22] Filed: Feb. 15, 1985

[51] Int. Cl.$^4$ ................................................ C07F 7/16
[52] U.S. Cl. ........................................ 556/472; 252/1; 252/188.31; 502/170; 502/200; 502/225; 502/343; 502/345
[58] Field of Search ................. 556/472; 252/1, 182, 252/188.37; 502/170, 200, 225, 343, 345

[56] References Cited

U.S. PATENT DOCUMENTS

| | | | |
|---|---|---|---|
| 2,380,995 | 7/1945 | Rochow | 260/607 |
| 2,380,996 | 7/1945 | Rochow | 260/607 |
| 2,380,997 | 7/1945 | Rochow | 260/607 |
| 2,420,540 | 5/1947 | Hubbell | 75/0.5 |
| 2,443,902 | 6/1948 | Ferguson et al. | 260/448.2 |
| 2,464,033 | 3/1949 | Gilliam | 260/448.2 |
| 2,466,413 | 5/1949 | Gilliam et al. | 260/448.2 |
| 3,446,829 | 5/1969 | Zock | 260/448.2 |
| 4,218,387 | 8/1980 | Maas et al. | 556/412 |
| 4,314,908 | 2/1982 | Downing et al. | 252/182 |
| 4,450,282 | 5/1984 | Ritzer et al. | 556/472 |
| 4,500,724 | 2/1985 | Ward, III et al. | 556/472 |

Primary Examiner—Paul F. Shaver
Attorney, Agent, or Firm—Eugene C. Trautlein

[57] ABSTRACT

An improved Direct Reaction process which comprises reacting an organohalide with an activated silicon composition, the improvement comprising maintaining the composition of the activated silicon so that it comprises, based on the amount of silicon, 0.05–10 wt. % catalyst; an effective amount of promoter, and 0.001–0.1 wt. % tin, wherein the promoter to tin ratio is 10–250. Activated silicon compositions and methods for selecting a catalyst composition also are provided.

8 Claims, No Drawings

TIN CONTAINING ACTIVATED SILICON FOR THE DIRECT REACTION

FIELD OF THE INVENTION

This invention relates to organohalosilanes, and, more particularly, to the synthesis of organohalosilanes such as methylchlorosilanes and to an activated silicon composition used in this synthesis.

BACKGROUND OF THE INVENTION

The Direct Reaction Generally

Organohalosilanes, particularly methylchlorosilanes, are used extensively for making silicone gums, resins and fluids. The basic process for producing the organohalosilanes is a one-step reaction of an organohalide with suitably-activated silicon metal. The process, known variously in the art as the Direct Process, the Direct Synthesis, the Direct Reaction, or the Rochow Synthesis (hereinafter "Direct Reaction"), was first disclosed in Rochow U.S. Pat. No. 2,380,995.

The Direct Reaction is conventionally performed in a gas-solid reactor, such as a fixed bed, a stirred bed, or a fluidized bed reactor. Such reactors typically include means for intermittently adding quantities of silicon, catalyst, and the promoters used in the reaction and described below.

An organohalide, as used herein, is a compound of general formula RX, wherein R represents a saturated or unsaturated aliphatic or aromatic hydrocarbon radical, such as alkyl, vinyl, or phenyl, and X is a halogen atom. Examples are methyl chloride, ethyl bromide, phenyl chloride, and vinyl chloride. The preferred organohalide in most cases is methyl chloride.

Activated silicon in the art refers to silicon into which a catalyst has been incorporated, as well as other materials such as promoters and the like. The term catalyst refers to an element, typically copper or silver, their compounds, or other metals known to catalyze the Direct Reaction. Such metals fuse with and diffuse into silicon to form an alloy or solid solution, the phase which is reactive with organohalides. Thus, with such alloys or solid solutions the Direct Reaction with methyl chloride may be conducted at temperatures substantially less than 400° C., the temperature at which the uncatalyzed Direct Reaction is initiated.

The chemistry of the Direct Reaction, however, is somewhat complex. For example, when the organohalide is methyl chloride (MeCl), the catalyst is copper, and the process is conducted as generally described in U.S. Pat. No. 2,380,995, a mixture of products is produced: $HSiCl_3$, $MeHSiCl_2$, $Me_2HSiCl$, $SiCl_4$, $Me_3SiCl$, $MeSiCl_3$, $Me_2SiCl_2$, $Me_xSi_2Cl_{6-x}$ ($0 < x < 6$, x is an integer), and, as well, a number of disilamethanes, siloxanes, and hydrocarbons.

When high levels of the copper catalyst are used, cracking, i.e., production of alkenes and HCl tends to become a problem. These cracking products are not desired products as they tend to contaminate the reaction bed and shorten its life.

Generally, $Me_2SiCl_2$ is considered to be the preferred product. To provide an evaluation of the efficacy of a particular application of the Direct Reaction, the performance, therefore, is generally measured by the reaction rate and the preference for $Me_2SiCl_2$. The reaction rate is usually defined as the quantity of raw material reacted per unit time, e.g., gm Si reacted per kg Si in the reactor per hour, percent Si reacted per hour, or gm MeCl reacted per gm Si in the reactor per hour. The preference for $Me_2SiCl_2$ is often referred to as its selectivity, defined generally as a gravimetric ratio, wt % $Me_2SiCl_2$/wt % $MeSiCl_3$, usually abbreviated D/T.

It is also known that small amounts, typically less than 1 wt %, of certain elements, e.g., Zn, Sb, Bi, Cd, Hg, and As, enhance the selectivity to $Me_2SiCl_2$, as well as the rate of the Direct Reaction. For example, U.S. Pat. No. 2,464,033 discloses that the presence of zinc at the preferred levels of 0.05-0.5 wt % in the mixture of silicon and copper yields higher D/T values. These elements are not considered catalysts in the temperature range of interest in the commercial practice of the Direct Reaction, viz., 270°-350° C. Rather, these are termed promoters. Zinc, as the metal, or the anhydrous chloride, oxide, or carbonate, is the preferred promoter.

Typically, an initial induction period is observed after the reaction gas is introduced into the reactor. Depending on operating conditions, an interrupting induction period often is observed as additional quantities of activated silicon, catalyst, and promoter are added. During these induction periods, the rates and selectivities are lower than those attained during steady-state operation.

The state of the art in the catalysis of the Direct Reaction is discussed in the following: W. Noll "Chemistry and Technology of Silicones", Academic Press, N.Y. (1968); A. Petrov, et al., "Synthesis of Organosilicon Monomers", Consultants Bureau, N.Y. (1976); R. J. H. Voorhoeve, "Organohalosilanes: Precursors to Silicones", Elsevier, N.Y. (1967) and reviews; J. J. Zuckerman, Advances in Inorganic and Radiochemistry, vol. 6 (1964) pp 383-432; A. G. MacDiarmid (Editor), "The Bond to Carbon", vol. 1 Marcel Dekker, Inc., N.Y. (1968) C. Eaborn and R. W. Bott, pp 105-536; W. Buechner, "Organometallic Chemistry Reviews", Library 9, pp 409-431. Both the choice of copper catalyst and the method of its incorporation with silicon are known to influence the D/T ratio and the rate of the Direct Reaction. Accordingly, there have been many attempts to identify the chemical and physical characteristics of the catalyst critical to reproducibly carrying out the Direct Reaction at an optimal rate and selectivity.

Enhanced, reproducible performance by a catalytic composition has been ascribed in the art to a variety of factors: Cement vs. non-cement catalyst, the presence or absence of trace elements in addition to known promoters, and surface area and particle size. Often these factors are considered dominant factors. Nevertheless, enhanced, reproducible performance in the Direct Reaction has not been achieved in commercial practice.

Typically, solving one problem exacerbates another. Increasing temperature, for example, increases rate but decreases selectivity. Increasing the amount of catalyst also increases rate, but eventually that causes excessive cracking and carbon formation.

Induction periods and shortened bed life in the gas-solid reactor previously have contributed to lower overall efficiency of commercial processes as well.

Catalytic Compositions—Cement Catalysts And Presence Of Trace Elements

U.S. Pat. No. 2,380,996 mentions that copper metal, copper oxides and copper salts are suitable catalysts for the Direct Reaction, but it does not describe in detail the preferred preparation of these catalysts, or the preferred chemical and physical properties of catalysts which produce optimum rate and selectivity. It is known, however, that commercially available cuprous oxide, cupric oxide and cupric hydroxide show far less catalytic activity in the Direct Reaction than do mixtures of copper metal, cuprous oxide, and cupric oxide produced by cementation processes.

In cementation, an aqueous, copper-bearing solution is contacted with Fe, Al, Zn, or another metal higher in the electrochemical series than copper. The copper precipitates, and the metal dissolves. Copper catalysts prepared by cementation processes are known as cement catalysts. Those not so prepared are non-cement catalysts.

For example, U.S. Pat. No. 2,443,902 discloses that D/T increases substantially when the copper catalyst is cement copper rather than cupric oxide. The particular cement copper set forth is that obtained in accordance with U.S. Pat. No. 2,420,540. A powder is produced by subjecting the unrefined, wet cement copper to a hot grinding process in an environment that is at least somewhat oxidizing in nature (column 6, lines 1-2). Its essential features are a friable, metallic copper core surrounded by surface films of cuprous oxide, a high surface area, and a particle size distribution of 2-10 microns.

British Pat. No. 1,201,466 states that the copper precipitate produced by zinc cementation of copper salts, as opposed to iron cementation, is a superior catalyst for the Direct Reaction. The basis of this superior performance was attributed to the excess zinc retained in the precipitated copper. However, no optimum concentration range of zinc in the copper catalyst was disclosed as desirable or as contributing to advantageous rate and selectivity.

German Pat. No. 2,811,853 claims that the finely-divided, cement copper catalyst produced by its process is superior to that made by the process of British Pat. No. 1,201,466. This discloses a process characterized by mechanical activation during unalloyed steel cementation. The chemical and/or physical properties responsible for the improved performance of the copper catalysts are not disclosed.

European Pat. No. 0,057,383 also discloses cement copper catalysts for the Direct Reaction. These are prepared by agitating fine, predominantly iron-containing, cast materials, e.g., turnings and shavings, in an acidic, copper-containing solution. The crude precipitate ultimately is washed with acids to reduce its iron content and increase its porosity.

Although it was known that such cementation processes yield impure copper catalysts, it was unclear which impurities should be present. For example, East German Pat. No. 21,380 describes the preparation of a highly active copper catalyst. Finely divided copper powder is leached repeatedly with hot, 20% aqueous, oxygen-free hydrochloric acid to remove impurities. The leached product finally is dried in a reducing atmosphere and is not exposed to air before use. Similar leaching of acid-soluble, metallic impurities from silicon and from a silicon-copper alloy is described, respectively, in German Pat. No. 823,540 and USSR Pat. No. 129,657. Leaching removes acid-soluble metals such as Fe and Al.

The teachings of those patents regarding purification of starting materials and its beneficial effect on activity and selectivity of the direct synthesis, however, are at variance with other publications. In L. Malysheva et al., 49 Russian *Journal of Applied Chemistry* 2245-2249 (1976), it is reported that highly pure copper shows the lowest catalytic activity in the Direct Reaction because of its low concentration of promoting impurities. The impurities which are depleted in the highly refined copper are As, Sb, Ni, Ag, Sn, and P. Copper catalysts of lesser purity, however, also may show low catalytic activity if they contain an excess of inhibiting impurities, e.g., Pb and S.

However, M. Bhasin, 34 *Journal of Catalysis* 356–59 (1974), discloses that the mere presence of sulphur is not inhibitive. Cement copper catalysts are conventionally precipitated from an acidic sulphate solution and do contain sulphur in the form of sulphate.

Bhasin also disclosed that, for two cement copper catalysts of very similar bulk chemical composition, surface area, and mean particle size, the difference in their performance was attributable to the higher surface concentration of Pb in the poorly-performing catalyst. There was no significant difference in the surface concentration of other relevant impurities, e.g., As, Fe, and Sn. N. Lobusevich et al, 10 *Bulletin Academy of Sciences, USSR, Division of Chemical Science* 1613–1621 (1963), similarly observe a depressing effect on the reaction rate and selectivity to $Me_2SiCl_2$ by the presence of 0.1 wt % Pb in the copper-silicon alloy used for the Direct Reaction.

In a separate publication cited in 56 *Chemical Abstracts*, 10971 (1961), N. Lobusevich et al. report no improvement in the rate of the Direct Reaction when low levels of Al, Ca, Fe, Sn, or Ti are added to the silicon-copper alloy.

Accordingly, comparing the teachings of East German Pat. No. 21,380, German Pat. No. 823,540 and USSR Pat. No. 129,657 on the one hand, and those of the publications of Malysheva, Bhasin and Lobusevich on the other, the prior art is unclear whether the starting silicon and copper catalyst should be purified before use in the Direct Reaction. It also is unclear which impurities should be specifically depleted or removed and which retained.

In particular, nothing is taught about the desirability of the presence of low levels of tin. R. Voorhoeve, ORGANOHALOSILANES p. 135 (1967), however, concludes that "the effect of tin is uncertain. It has been reported to have no effect, but since the alloys used in these experiments were found, on subsequent analysis, to have contained antimony, the statement is of little value. There have been some indications that tin decreases the activity of the alloy". Moreover, it was shown by R. Voorhoeve et al., 82 *Recueil des Travaux Chimiques des Pays-Bas*, 605–615, (1963), and by K. Nishikawa et al., 48 *Chem. Abstr.* 10055f, (1954), that the use of tin as a catalyst, in place of copper, favored the formation of $MeSiCl_3$ rather than $Me_2SiCl_2$. The disclosures of Voorhoeve and Nishikawa reported the use of tin at concentrations of 6–17 wt %, based on the total weight of silicon used.

To further complicate the matter, in contrast to U.S. Pat. Nos. 2,420,540, 2,443,902, and East German Pat. No. 21,380, U.S. Pat. No. 4,218,387 teaches that the copper catalyst for the Direct Reaction must be prepared in an oxidizing environment. The copper powder is partially oxidized with oxygen at a reduced partial pressure compared with that of air. The resulting catalyst has an average particle size between 0.1–100 microns, contains 3–100 wt % cuprous oxide and shows enhanced selectivity to $Me_2SiCl_2$. Reducing gases, such as CO or $H_2$, are specifically contraindictated during the oxidation process. It also is taught that electrolytically produced copper powders, powders produced by atomization of copper melts, those formed by chemical reduction of copper salts, and powders precipitated during the disproportionation of cuprous salts are suitable starting materials. However, the limiting levels of promoting and inhibiting trace metals tolerable in the catalyst for the realization of advantageous rate and selectivity are not defined in this patent.

Many of the commercial copper catalysts used in the Direct Reaction over the years have contained impurities such as tin in varying amounts. Likewise, commercial grades of silicon used in the Direct Reaction often contain some level of tin as an impurity. Although it was known that a promoter was desirable, no benefits were recognized from controlling the amounts and relative amounts of tin and promoter in the activated silicon.

Catalytic Compositions—Surface Area And Particle Size

The importance of surface area and particle size distribution of the catalyst to optimum D/T and rate is stressed in the prior art. Surface area measurements are made by the method of Brunauer, Emmett and Teller using nitrogen adsorption as described in 60 *Journal Amer. Chem. Soc.* 309-19 (1938). This method conventionally is referred to as the BET method. Values are reported in units of area per unit weight, e.g., meters squared per gram ($m^2$/gm). Particle size is measured in microns by any of a number of methods recommended in 7 METALS HANDBOOK® NINTH EDITION, POWDER METALURGY 209-32 (Coordinator E. Klar) (Am. Soc'y for Metals, Metals Park, Ohio 1984).

For example, cement copper catalysts prepared by the process of European Pat. No. 0057383 have high surface area, i.e., between 10 $m^2$/gm and 100 $m^2$/gm. In that patent, it was stated that the copper catalysts must possess large surface areas in order to display high catalytic activity (page 1, lines 8-14). Large surface area would be produced by a combination of small particle size and high porosity.

The importance of surface area and particle size distribution to optimum D/T and rate also is taught by U.S. Pat. No. 4,450,282. This patent states (column 7, lines 26-68 and column 8, lines 1-68) that the one criterion the catalyst must meet in order to show high selectivity to $Me_2SiCl_2$ is that the surface area of the catalyst must be at least 3.5 $m^2$/gm, should not exceed 12 $m^2$/gm, and is preferably 3.7-8 $m^2$/gm. The concentrations of chloride, sulphate, iron, lead, tin, and water in the catalysts are less important criteria for the obtention of advantageous selectivity. The relative amount of copper metal, cuprous oxide, and cupric oxide is also not an important measurement, nor is the apparent density or air permeability of the catalyst powder. If most of the values of these properties, that is, trace and bulk chemical composition, apparent density, and air permeability, are outside the preferred limits, the catalyst can still be used to obtain high reaction rate and optimum selectivity. It is necessary only that the surface area of the partially oxidized copper catalyst (preferably cement copper) be greater than 3.5 $m^2$/gm, that the particles have a particle size distribution between 0.7-35 microns and that the predominant particle size range of the particles is 4-7 microns.

Another patent, U.S. Pat. No. 2,466,413, claims the following particle size distribution for powdered metallic (preferably copper) catalysts useful in the selective direct synthesis of $Me_2SiCl_2$ 100 wt % of the particles are less than 420 microns, 80-100 wt % are less than 44 microns and 60-100 wt % are smaller than 15 microns.

None of these patents which disclose the desirability of a specific range of surface areas and/or particle sizes teaches that the tin level of the catalyst or activated silicon is critical to the obtention of high rate and optimum selectivity as well as to the quantity of higher boiling (greater than 70° C.) residues, chiefly disilanes, disilamethanes and disiloxanes, formed.

Catalytic Compositions—Induction Periods

It is known that the initial induction period is reduced greatly by the presence of aluminum or zinc or by the use of high surface area, powdered copper catalysts (see R. VOORHOEVE, ORGANOHALOSILANES 126-27, 250-51; and R. Mueller et al., 61 *Chem. Abstr.* 679b (1964)). Voorhoeve attributed the existence of the induction period to the time required to generate $Cu_3Si$, the commonly accepted catalytic phase. Mueller et al. concluded that the induction period was associated with the formation of $AlCl_3$ and $FeCl_3$ in the activated silicon. Frank (Doctoral Dissertation, Univ. of Colo., Boulder, 1984) observed that the presence of 0.5 wt % zinc in $Cu_3Si$ shortened, but did not eliminate, the induction period. Maas et al., U.S. Pat. No. 4,218,387, reduced the induction period by initiating the Direct Reaction at 360° C. and thereafter reducing the temperature 10-15° C. per hour until the desired reaction temperature is attained.

Catalytic Compositions—Bed Life

The overall efficiency of a continuous Direct Reaction process is directly related to the life of the bed in the gas-solid reactor. Obviously, the longer the bed life, the less frequently the process must be stopped to change the bed. Bed life itself is limited by the buildup of chloride reaction products with metal impurities, such as Al, Fe and Ca, carbon, and organic cracking products. Because the chlorides either tend to vaporize or get blown out, the carbon and organic cracking products are the primary contaminants in the bed. Lower levels of Cu reduce cracking. Extending the bed life by reducing the level of Cu catalyst, however, has been constrained by the lower limit of catalytic activity known in the art.

Summary

The literature discussed above provides varying, and sometimes contradictory guidance on selecting a copper catalyst and incorporating promoters and other trace metals to obtain high rate and selectivity in the Direct Reaction. Accordingly, and despite the substantial amount of prior work in this area, there is substantial room for improvement in carrying out the Direct Reaction in a facile manner. Substantial increases in the rate and selectivity would be thus highly desirable, as well as increased reproducibility. It would be highly useful to be able to carry out the Direct Reaction without encountering any significant induction periods, which seem characteristic in this process, causing a decrease in the overall performance. In addition, and importantly, it would be extremely helpful to be able to carry out the Direct Reaction in such a fashion that both the amount of "heavies"(i.e.—disalanes) produced as by-products are reduced and, as well, the proportion of the disilane species in the heavies which cannot be converted by reaction with hydrochloric acid to form the desired product, viz., Me$_2$SiCl$_2$. The capability of using a reduced amount of copper catalyst without loss of performance would not only improve the economics, but would also reduce the degree of cracking which takes place, thereby increasing the bed life. Using less Cu, of course, lessens the disposal problems associated with the spent catalyst.

OBJECTS OF THE INVENTION

Thus, it is a principal object of the present invention to provide a facile process for carrying out the Direct Reaction in a consistent and reproducible manner.

Another object is to provide a Direct Reaction in which the rate is high and reproducible without adversely affecting selectivity and bed life.

A further object of the invention is to provide a Direct Reaction in which the selectivity is high and reproducible without adversely affecting rate.

A still further object of this invention is to provide a Direct Reaction which produces less heavies and heavies having a more desirable disilane distribution.

A further object is to provide a Direct Reaction in which the amount of heavies produced is decreased without substantial decrease in performance.

Another object is to provide a Direct Reaction in which any induction period is substantially reduced or eliminated.

Another object is to provide a Direct Reaction in which the bed life is increased.

A further object is to provide an activated silicon composition for particular Direct Reactions which may be employed to achieve the objects stated herein.

Other objects of the present invention will become apparent from the following description.

SUMMARY OF THE INVENTION

The present invention is, in general, predicated on the discovery that carrying out the Direct Reaction utilizing a particular tin level and particular promoter to tin ratio provides substantially improved rates and selectivity and other advantages as compared to the state-of-the-art processes. The manner in which these objects are achieved will be fully described in the ensuing detailed description of the present invention.

DETAILED DESCRIPTION OF THE INVENTION

The Direct Reaction Generally

The Direct Reaction is conventionally performed in a gas-solid reactor such as a fixed-bed, a stirred-bed, or a fluidized-bed reactor. Descriptions, designs and operational considerations pertinent to these reactors are given in L. DORAISWAMY & M. SHARMA, HETEROGENEOUS REACTIONS: ANALYSIS, EXAMPLES AND REACTOR DESIGN, GAS SOLID AND SOLID-SOLID REACTIONS (Vol. 1) (John Wiley & Sons, New York 1984).

Activation, as previously discussed, and as is known, is the process of incorporating catalyst, and if desired, other auxiliary agents, into the silicon. This may be carried out in the same reactor used for reaction of the organohalide, or in a separate reactor. In the latter situation, the activated silicon is typically and desirably transported to the reaction reactor in an anhydrous, non-oxidizing atmosphere.

Activation may be accomplished by, for example, solidifying a melt containing catalytic copper and silicon and comminuting the solid into particles, by heating particles of silicon and catalytic copper as described in U.S. Pat. No. 2,380,995, or preferably by heating mixtures of catalyst, preferably a mixture of copper oxides and silicon in the presence of hydrogen and/or hydrogen chloride (see, e.g., U.S. Pat. Nos. 2,380,997 and 4,314,908), or by heating copper salts (e.g., cuprous chloride, copper formate) and silicon (see, e.g., U.S. Pat. No. 2,119,808 and R. Voorhoeve et al., 4 *Journal of Catalysis* 123–133 (1965)) to temperatures between 300°–400° C. Various other catalysts and methods of activation are known in the art and have been described in the above mentioned monographs and reviews.

In its preferred form in accordance with the present invention, the Direct Reaction is conducted in a fluidized-bed reactor utilizing copper-activated silicon, a zinc promoter and gaseous organohalides. The reactor may have a single nozzle or multiple nozzles for continuous introduction of gaseous organohalide. A means of continuous or intermittent addition of comminuted solids, that is, silicon-copper alloy or copper-activated silicon or a contact mixture of silicon particles and powdered copper catalyst, plus zinc promoter, also is provided. Means for continuous removal of gaseous reaction products, unreacted organohalide, and elutriated fine particles should also desirably be provided. Conventional techniques and equipment are known and may be utilized.

Conventional means of separating the solid particles from the hot gases (e.g., with cyclones and/or filters) and a means of cooling and condensing the hot product mixture in a vessel separate from, but connected to the fluidized-bed reactor may also be provided, if desired. Other operational details relevant to the fluidized-bed reactor and the separation and recovery of product are well known to those skilled in the art, and thus will not be fully described herein.

Steady-state operation is typically defined as the condition in a Direct Reaction process in which the reaction rate and selectivity have increased from their initial level to a level which (provided the supply of activated-silicon, promoter and methyl chloride are continued at their preferred rates) can be retained for an extended reaction period. For batch fluidized-bed Direct Reactions, Voorhoeve (ORGANOHALOSILANES 161–172) has shown that steady-state extends from approximately 10 through approximately 50 percent silicon conversion.

In accordance with the present invention utilizing the preferred activated silicon achieves a high reaction rate and selectivity. For the preferred case of methyl chloride as the organohalide, reaction rates greater than 1.0 wt % Si converted per hour and selectivities, D/T, greater than 10, preferably rates greater than about 2.0 wt % Si converted per hour and a D/T of greater than about 18 may be attained at the steady-state condition. The obtention of these steady-state rates and selectivities may be achieved in the temperature range of from about 270 to about 350° C., the temperature range generally considered to be of interest for the commercial practice of the Direct Reaction.

The principal products of the Direct Reaction, with methyl chloride as the organohalide, as previously noted, are HSiCl$_3$, MeHSiCl$_2$, Me$_2$SiHCl, Me$_3$SiCl, SiCl$_4$, MeSiCl$_3$, Me$_2$SiCl$_2$, Me$_x$Si$_2$Cl$_{6-x}$ (0 < x ≦ 6, x is an interger), MeCl$_2$SiCH$_2$SiClMe$_2$, MeCl$_2$SiCH$_2$SiCl$_2$Me, Me$_2$ClSiCH$_2$SiClMe$_2$, various methylchloro-disiloxanes and methylchlorotrisilanes. Of the predominant disilanes, $Me_3Si_2Cl_3$ and $Me_2Si_2Cl_4$, the former generally is preferred in that it can be converted with HCl to $Me_2SiCl_2$. In the above list, the compounds following $Me_2SiCl_2$ all have normal boiling points greater than 70° C. and are typically included in the category, termed the higher boiling fraction.

The preferred compound from the Direct Reaction using methyl chloride is, as noted, $Me_2SiCl_2$. Pursuant to this invention, $Me_2SiCl_2$ comprises at least 80 wt % and, preferably, at least 85 wt % of the reaction products.

By the use of this invention, the typical level of certain of the byproducts are as follows: $MeSiCl_3$ is at most 5 wt % of the reaction products, $MeHSiCl_2$ is at most 1 wt %, $Me_3SiCl$ is at least 1.0 wt % and the higher boiling fraction is at most 8 wt %. Indeed, the process of this invention can generally reduce the quantity of higher boiling fraction to less than about 5 wt %.

The preferred activated silicon of this invention comprises quantities of preferred catalyst, preferred promoter and preferred silicon, with or without added tin, such that the tin level in the resulting mixture falls broadly in the range 0.001–0.1, preferably 0.001–0.01 wt %, based on the weight of silicon used, and the gravimetric ratio of promoter/tin is generally about 10 to about 250, preferably about 10 to about 100, and most preferably 20 to about 50.

The removal of promoter and tin by elutriation, evaporation and volatile compound formation can be such that the composition of the activated silicon falls outside the desired ranges causing concomitant reduction in the rate and D/T. Consequently, it will generally be desirable to add promoter and tin, in one or more of the forms described hereinafter, to the reactor and/or to the activated silicon feed to maintain both the desired promoter/Sn ratio and the total promoter and tin concentration.

The composition of the activated silicon and other materials added to the reactor will be known relatively precisely. The critical quantities and ratios, however, are those which actually exist in the reactor or at the catalyst surface at any given time. Samples may be withdrawn periodically from the reactor bed to determine those values.

Because of the imprecision associated with sampling solid mixtures, however, reactor bed samples alone may not reflect accurately the bed composition. Thus, samples from the cyclone and filter also are collected and analyzed periodically. A mass balance around the reactor then may be calculated to aid in interpreting the data from bed samples.

Moreover, because of the variance in the determination of the bed composition different reactors may appear to have different optimum activated silicon compositions. However, these optimum compositions will fall within the ranges specified by this invention.

It is possible to perform the Direct Reaction of this invention by allowing the promoter/Sn values to fall outside 10–250 and then to inject periodically a massive quantity of promoter to increase the promoter/Sn ratio to well above 50, and even beyond 250. The reaction may be then allowed to proceed with tin-containing activated silicon until rate and selectivity first improve and then deteriorate with time. A massive promoter addition then may be repeated, allowing the promoter/Sn ratio to cycle once more from very high to very low values. Although large additions of zinc promoter, especially those which give local or overall zinc concentrations in excess of 1.00 wt.%, are deleterious to bed fluidization and heat removal from the reactor, under such procedures some improvement over the prior art processes is possible. However, it is more preferable to carry out the Direct Reaction pursuant to this invention by maintaining the promoter/Sn, total promoter and total Sn within the limits defined herein throughout essentially the entire reaction to maximize the benefits provided by this invention. Particularly if preferred ranges are essentially observed, rates over 2.0 wt % Si and selectivities greater than 18 are obtained.

As noted, commercial silicon and catalysts, particularly cement copper, used in the Direct Reaction have contained trace amounts of tin. It also is known in the art that cement copper in amounts from 4 to 10 wt %, perhaps as low as 2 wt %, based on silicon, may be loaded. There is some indication in U.S. Pat. No. 4,450,282 (Example 2) that loadings as low as 1 wt % may be used. It is not clear from that patent, however, whether that in fact was, or can be done. Regardless, it is likely that activated silicon compositions have been used which contain effective amounts of promoter and tin in amounts from 0.001–0.1 wt %.

It also might be expected that through accident, in using such cement coppers and in maintaining effective amounts of promoter, the Direct Reaction would have been conducted commercially not only with the amount of tin, but with the ratio of promoter to tin falling within the broad scope of this invention. If such had been the case, however, enhanced and reproducible performance would have been observed. That observation not having been made, it may be assumed that known Direct Reaction processes, if practiced within the scope of this invention, were done so in a transitory manner so that the benefits derived therefrom could not be sustained.

Silicon

The silicon employed in the Direct Process is commonly a technical grade material containing 90–99 wt % silicon. E. Rochow, in 1 COMPREHENSIVE INORGANIC CHEMISTRY 1328–29 (J. Bailar ed. 1969) (Silicon), reports the following composition for commercial silicon typically used in the Direct Reaction: Si=98.53 wt %, Fe=0.56 wt %, Al=0.31 wt %, Ca=0.12 wt %, Mn=0.04 wt %, Ti=0.02 wt %, other metals=0.08 wt %, and O=0.35 wt %. The preferred values for the process of the instant invention are Si=98.5 wt % minimum, Al-0.20-0.4 wt %, Fe=0.3-0.6 wt %, Ca=0.01-0.15 wt %, Ti=0.03-0.06 wt %, and Mn=0.005-0.01 wt %. The category "other metals", includes elements such as Mg, Zn, P, Cu, Cr, V, Se, Bi, Sb, and Pb. N. Lobusevich, 49 Russian Journal of Applied Chemistry, No. 10, p. 2168–2174, (1976), has identified these and other trace metal impurities commonly present in commercial grade silicon.

Of these trace metals, lead is among the most critical. Its concentration should generally not exceed about 0.001 wt % of the silicon. The copper concentration is not critical. Copper is usually present within the range 0.002–0.01 wt %. The zinc concentration is typically less than 0.002 wt %. The tin concentration in conventional silicon usually is negligible and less than 0.0005 wt %. A specially preferred silicon for this invention is that which contains a concentration of up to 0.1 wt % Sn and a zinc concentration such that the Zn/Sn gravimetric ratio falls within the range 10–250, preferably 10–100.

A broad range of silicon particle sizes, e.g., 28×D mesh (i.e., no more than 500 microns) may be used in the synthesis. It is preferred, however, that the silicon particles be smaller than about 48 mesh (i.e., less than 300 microns) and larger than about 325 mesh (i.e., larger than 45 microns). Smaller particle sizes tend to contribute to good fluidization of the bed and assist heat transfer. The particle size range employed in any given reaction depends on the size of the reactor and the scale of the synthesis. In laboratory experiments, the preferred particle size range has been found to be 65×150 mesh (i.e., 104–208 microns), but this distribution is not considered essential for the success of the synthesis.

Preformed metal silicides such as those of iron, calcium, magnesium, and copper also may be employed in the synthesis either as individual phases or admixed with elemental silicon.

Catalysts

The preferred catalysts for the process of the instant invention are powdered metallic copper, any anhydrous copper compound, or mixtures thereof. Metallic silver, its compounds and their mixtures, however, also are known to be effective catalysts.

Examples of copper compounds suitable for use individually or in mixtures are cuprous oxide, cupric chloride, copper nitride, copper carboxylates such as copper formate and copper acetate, intermetallic copper compounds such as lead-free bronzes and brasses, and copper acetylacetonate. This, however, is not a restrictive or exclusive list.

Copper compounds specifically contraindicated are those such as copper phosphide, copper sulfides and inter-metallic compounds of lead and copper. These compounds will introduce into the Direct Reaction intolerable levels of compounds or elements known to exert a negative effect on the rate and/or selectivity.

A preferred copper catalyst is a powdered mixture of copper, cuprous oxide and cupric oxide such as that which is produced by cementation, by atomization and partial oxidation of molten copper, by the partial oxidation of electrolytically or chemically produced copper metal, or by the incomplete reduction of cupric oxide. Although cement copper catalysts may be preferred, however, non-cement catalysts can be used as well.

The amount of copper required to activate the silicon is usually less than about 10% by weight of the silicon used. Copper in amounts greater than 10 wt % are detrimental to the Direct Reaction. In general, amounts of from about 0.05 to 3 wt % have been found to be optimal. An increase in the amount of copper beyond that range, up to 10 wt %, has a negligible effect of the desired results of the Direct Reaction. Concentrations below 0.05 wt % also are useful, but may give erratic results. The present invention, however can use advantageously a copper level of about 1 wt % or less. At those low levels, cracking products are reduced and the life of the bed may be extended thereby at least 25%.

When the copper catalyst employed contains tin, it is essential that the catalyst use level be so chosen that the tin concentration falls within the broad limits defined above. For example, if the tin concentration of a copper catalyst is 0.25 wt %, the usage of that catalyst must be less than 4 wt % of the silicon in order to satisfy the tin criterion. Accordingly, the silicon and promoter also must not contain too much inherent tin. If the amount of the copper catalyst used is less than that amount required to meet the tin specification, then additional tin should be added as necessary. Several techniques for tin addition will be described hereinafter.

A customary practice in the art is the selection of cement copper catalysts based on criteria such as total copper content, the proportions of metallic copper, cuprous oxide and cupric oxide, the content of lead, iron, aluminum, and water, particle size and particle size distribution, and BET surface area. Thus, the total copper content of a cement catalyst can be anywhere within the range 77 to 87 wt %, and is preferably 83–87 wt %. The total metallic copper content of the cement catalyst generally varies from 10–20 wt % and is preferably 15 wt % as a maximum. It is also customary to select catalyst with a broad cuprous oxide content of 30–50 wt %, more narrowly 30–40 wt %, and a cupric oxide content that is broadly 35–60 wt % and narrowly 45–60 wt %.

Generally, the content of lead is a critical standard. A maximum concentration of 0.07 wt % defines the broad range. A preferable range is 0.005 wt % maximum. The iron content of the cement copper catalyst varies from 0 to 2.5 wt %, but is preferably 0.25 wt % maximum. In the same way, the aluminum content varies from 0 to 0.50 wt % and is preferably 0.2–0.3 wt %. The water content can vary from 0–0.75 wt % and is preferably 0.5 wt % maximum.

When a cement catalyst is used, it is generally preferred that the cement copper catalyst be composed of particles in the range 2–10 microns. However, particles up to a maximum of 44 microns are acceptable. A minimum BET surface area of 1 $m^2/gm$ is generally acceptable.

Despite these generally accepted broad and narrow criteria for the selection of cement copper catalysts, it also is known in the art that, with the exception of the lead standard, these criteria are not the important ones for the rate and selectivity of the Direct Reaction and are of no predictive value in assessing the performance to be expected from an activated silicon. It will be shown hereinafter that, by the process of the instant invention, it is possible to arrive at empirical relationships which broadly predict the rate and selectivity to be expected when a tin-containing activated silicon is prepared and reacted according to the preferred conditions described herein. It will be also shown that non-cement copper catalysts and simple copper compounds are acceptable catalysts for the Direct Reaction as well, provided the reaction utilizes the tin level and the promoter/Sn ratio within the present invention.

Promoters

Promoters preferably are employed in the Direct Reaction so that both satisfactory rate and selectivity are both obtained. U.S. Pat. No. 2,464,033 discloses the use of metallic zinc, zinc chloride, and mixtures thereof to accelerate the activity of the catalyst as regards the rate of production and type of product produced (column 4, lines 33–35). Good results are stated to be obtained if the promoter, expressed in terms of zinc, is present, by weight, in an amount equal to from about 0.03 to less than 0.75 percent, preferably from about 0.05 to 0.5 percent based on the total weight of silicon used (column 4 lines 51–55). Cadmium, in the preferred concentration range of 0.06 to 3.75 wt %, is disclosed as a promoter in U.S. 3,446,829.

Although promoters are discussed widely, there is no consensus among those skilled in the art on the definition of a promoter. For example, two functional definitions are disclosed in the art. Voorhoeve (ORGANOHALOSILANES 132) defined a promoter as an additive which, if present in small or very small (less than 1 wt %) amounts, potentiates the action of the copper catalyst. DeCooker et al., 86 *Journal of Organometallic Chemistry*, 175-83 (1975), defined a promoter as a solid or liquid additive which, at reaction conditions, is converted to a stable metal chloride on the copper-silicon surface and potentiates the action of the catalyst by the formation of active centers of the type $SiCl_n$ ($n<3$).

Those functional definitions, however, generally will be satisfied by an element or compound (hereinafter "element" for simplicity) which improves the selectivity to the diorganodihalosilanes and meets the following criteria:

1. The element has either a hexagonal and/or rhombohedral crystal habit (see Table 1);
2. The element has an atomic size which allows for both substitutional and interstitial fit in the silicon lattice (see Table 1);
3. Individual atoms or clusters of atoms of the element occupy vacancies, voids and other defects on the surfaces and interfacial areas of the activated silicon;
4. The element and its metal halides show a strong tendency to concentrate at the surfaces and interfacial areas of the activated silicon;
5. The element stabilizes a specific range of copper (or silver) silicon surface atomic compositions thereby imparting definite structural and electronic characteristics to the reactive surfaces of the activated silicon;
6. The element and its halides are easily vaporized from the reaction zone;
7. The element shows an optimum value or range of values for its effect on the rate and selectivity of the Direct Reaction;
8. The optimum amount of the element required is related to the tin content of the activated silicon.

TABLE 1

| Promoter | Crystal Habit | Unit Cell Constants | Axial Ratio c/a | Covalent Radius | Atomic Radius |
|---|---|---|---|---|---|
| Zn | Hexagonal | a = 2.665Å, c = 4.947Å | 1.86 | 1.31Å | 1.38Å |
| Cd | Hexagonal | a = 2.979Å, c = 5.618Å | 1.89 | 1.48 | 1.54 |
| Hg | Rhombohedral | a = 2.999Å, α = 70°32' | | 1.49 | 1.57 |
| | Hexagonal | a = 3.463Å, c = 6.706Å | 1.94 | | |
| Sb | Rhombohedral | a = 4.507Å, α = 57°6.5' | | 1.38 | 1.59 |
| | Hexagonal | a = 4.307Å, c = 11.273Å | 2.62 | | |
| Bi | Rhombohedral | a = 4.746Å, α = 57°14' | | 1.46 | 1.70 |
| | Hexagonal | a = 4.546Å, c = 11.862Å | 2.61 | | |
| As | Rhombohedral | a = 4.131Å, α = 54°10' | | 1.19 | 1.39 |
| | Hexagonal | a = 3.760Å, c = 10.548Å | 2.81 | | |

In this invention, the preferred promoter is Zn, and it is used in an amount effective to increase rate and selectivity of the Direct Reaction, as known in the prior art. An effective amount, based on silicon, generally will be within the range of from about 0.05 to about 1.0 wt %. A preferred range is from about 0.05 to about 0.20 wt %.

Preferably, zinc is in the form of its metal or anhydrous chloride, oxide, or carbonate. It is also preferred, but not required for activation that in the mixture of solids (i.e., silicon, catalyst, promoter, and tin), the promoter have an average particle size, particle size distribution, and flow properties similar to those of the catalyst.

Tin

As has been previously set forth, the tin level, based on the weight of silicon, should be within the range of from about 0.001 to about 0.1%, preferably in the range of about 0.001 to about 0.01%.

Examples of the forms of tin which may be present in, or which may be added to the catalyst, silicon and/or promoter or to the reactor include, but are not restricted to, the following: metallic tin, stannous oxide, stannic oxide, stannous chloride, stannic chloride, copper stannate, tin carboxylates such as stannous formate and stannous acetate, organotin compounds such as methyltrichlorostannate, dimethyldichlorostannate and dibutyltin oxide, intermetallic compounds of tin such as $Cu_3Sn$, $Cu_{15}Sn_4$, and lead-free bronzes and brasses.

It is preferred that the tin additives be anhydrous. Preferred additives are metallic tin, stannous chloride, and stannous oxide.

Tin may be introduced into the activated silicon in a number of ways, all of which are considered effective for the realization of the benefits of this invention. These are: (a) the tin may be added to the molten silicon during its production, or it may be added to the comminuted solid used for the Direct Reaction; (b) the tin may be added to the catalyst during its manufacture, or it may be added separately to the catalyst later on; (c) the tin may be incorporated in the promoter during its manufacture, or it may be mixed separately with the promoter at a later stage; (d) the tin may be added separately to the mixture of silicon, catalyst and promoter prior to activation or reaction of said mixture or during the course of an activation or reaction already in progress; and (e) the tin may be transported into the Direct Reaction in the organohalide gas flow.

It is also preferred, but not required for activation that in the mixture of solids, the tin have an average particle size, particle size distribution, and flow properties similar to those of the catalyst.

Organohalides

The organohalide which may be employed in the present invention may be chosen from among those known to react with copper-activated silicon in the Direct Reaction, and may be represented by the general formula RX, wherein R represents a saturated or unsaturated aliphatic or aromatic hydrocarbon radical, such as an alkyl, vinyl or phenyl radical, and X represents a halogen atom. Suitable examples are methyl chloride, methyl bromide, ethyl chloride, vinyl chloride, and chlorobenzene. Methyl chloride is the preferred organohalide.

Standard commercial grade ethyl chloride of 99.6 wt % minimum purity is suitable as a starting material for the Direct Reaction. However, means to remove trace contaminants or to prevent the introduction of volatile impurities (e.g. - CO, $CO_2$, $O_2$, $CH_3OH$, $H_2O$, $SO_2$) which are known to interfere with the Direct Reaction could be provided, if desired. For large-scale Direct Reactions, wherein it is desirable to recycle the unreacted methyl chloride back through the fluidized bed reactor, it is advisable to purify the methyl chloride to remove hydrocarbons (e.g.—methane, isobutane) and nitrogen. These are not of themselves poisonous to the Direct Reaction. However, their presence does decrease the partial pressure of the methyl chloride available in the fluidized-bed reactor.

Other Reaction Parameters

The total amount of gaseous reactant (i.e., organohalide) employed in this invention must be, as a minimum, sufficient to fluidize the activated silicon particles and must, of course, be less than that flow which completely discharges or elutriates the copper-activated silicon particles from the bed before they are reacted. The minimum flow for fluidization may be readily computed from a knowledge of the gas densities, the density and particle size distribution of the copper-activated silicon particles, and the temperature of the reaction, as described for example in the monograph, D. Kunii and O. Levenspiel, *Fluidization Engineering*, (John Wiley & Sons, NY 1969). It is possible to operate the bed at many times this minimum flow and and still keep the reacting, activated silicon particles contained in the reactor in a fluidized state. For example, when a laboratory Direct Reaction is performed at atmospheric pressure and at 325° C. with methyl chloride and with an average silicon particle size of 149 microns, the minimum linear fluidization velocity has been found to be approximately 1.5 cm/sec. Operational values of 2-5 times this minimum flow are preferred.

In order to obtain optimum selectivity to the diorganodihalosilane and a satisfactory rate of reaction, it is desirable to keep the conversion of organohalide below 50 wt % per pass through the fluidized reactor. For the preferred organohalide, methyl chloride, it is known in the art (see VOORHOEVE, ORGANOHALOSILANES 237-239) that a methyl chloride conversion of up to about 35 wt % or so per pass is considered optimum.

The minimum temperature of the Direct Reaction is set by the initiation temperature of the reaction between the organohalide and copper-activated silicon. These temperatures are recorded in the above-cited monographs by Voorhoeve and Petrov. For example, at atmospheric pressure, the minimum temperature for methyl chloride reaction is about 290° C. At 4-5 atmospheres gauge, this temperature is reduced to about 260° C. The maximum acceptable temperature may be determined by the onset of organohalide pyrolysis. Such pyrolysis is usually accompanied by markedly increased formation of the less desirable organotrihalosilane, $RSiX_3$, and hydrocarbon byproducts.

Optimum temperatures are those which permit facile reaction and volatilization of the products without the complexities of pyrolysis. When the organohalide is methyl chloride, the content of $Me_2SiCl_2$ in the condensed reaction product is generally in excess of 80 wt % in the optimum temperature range. Additionally, the conversion of methyl chloride is maintained below 50 wt % per pass in the optimum temperature range. Accordingly, the operational temperature range when methyl chloride is the organohalide is 290-350° C. at atmospheric pressure and 260°-330° C. at 3-5 atmospheres.

As may be appreciated from the foregoing, the Direct Reaction may be carried out at atmospheric or at superatmospheric pressures. It is advisable to conduct the process under pressure since this increases the rate of the reaction and makes more efficient use of the organohalide and copper-activated silicon. Conventionally, a maximum pressure (measured at the top of the fluidized-bed reactor) of about 6 atmospheres gauge is used with methyl chloride. An optimum range of 3-5 atmospheres gauge allows the process to be operated at methyl chloride conversions of less than 50 wt % per pass, while affording stable and prolonged high selectivity to $Me_2SiCl_2$.

Finally, as noted above, the promoter to Sn ratio should be maintained from 10-250 for essentially the entire course of the Reaction. Although some performance benefits are obtained by maintaining that broad range for less than the entire reaction, for optimum performance, i.e., rates over 2.0 wt % Si and selectivities greater than 18, a narrower, preferred range, 10-100, should be maintained for essentially the entire course of the reaction. Moreover, if the especially preferred range of 20-50 is observed for essentially the entire course of the reaction, no interrupting induction periods will be observed and the initial induction period will be less than 3 hours.

Performance Advantages

In accordance with the present invention, substantial advantages may be achieved by appropriate selection and maintenance of the appropriate tin level and promoter/tin ratio. Considerable flexibility is provided so that the Direct Reaction may be varied as needed to achieve the performance for a particular application.

By applying the present invention, a wider range of catalyst types may be used. Thus, a catalyst that would otherwise provide inadequate performance, even as measured against prior standards, will provide enhanced and reproducible performance.

The subject invention also enables the Direct Reaction to be carried out at a high, reproducible rate, without adversely effecting the selectivity or bed-life of the Reaction. The selectivity also may be improved and made reproducible without decreasing rate. That may be accomplished by maintaining the tin level and promoter to tin ratio within the broad limits specified above. Specifically, in the case of methyl chloride, rates and selectivities greater than 1 wt % Si and 10, respectively, may be obtained. If the preferred tin level of 0.001-0.01 wt %, the preferred Zn level of 0.05-0.20 wt %, and preferred Zn to Sn ratio of 10-100 are maintained for essentially the entire course of the Reaction, reproducible rates and selectivities greater than 2 wt % Si and 18, respectively, may be achieved.

Similarly, by maintaining the broad ranges the heavies will be less than 8 wt % of the products, generally less than 5 wt %, and the $Me_2Si_2Cl_4$ to $Me_3Si_2Cl_3$ distribution will be improved without substantially decreasing performance.

Moreover, if the preferred tin and Zn levels and the especially preferred Zn to Sn ratio of 20-50 is maintained, the initial induction period will be less than 3 hours and there will be no interrupting induction periods during the Reaction.

The bed life also may be extended by at least 25%. That may be accomplished by maintaining the preferred tin and Zn levels and the especially preferred Zn to Sn ratio and by reducing the amount of copper catalyst used to the especially preferred range of 0.05–1.0 wt %. Lower copper levels reduce the amount of carbon and cracking products produced, the primary contaminants which reduce bed life. At the same time, lower copper levels reduce the disposal problem associated with spent beds.

Finally, it should be noted that when the copper, Zn, and Sn levels and the Zn to Sn ratio are maintained within the especially perferred ranges, all of the above benefits generally will be obtained.

EXAMPLES

The following Examples illustrate the preferred embodiments of the instant invention. These are not intended to limit the scope of the invention; rather, these are presented merely to facilitate the practice of the invention by those of ordinary skill in the art.

Reactors Used And Analyses

Two reactors were used in the following Examples. Reactor A is a conventional Vycor® fluidized-bed reactor of overall length 91 cm and internal diameter 3.2 cm. A sintered glass frit at the base of the reactor supports the bed of silicon or activated silicon particles and disperses the gaseous organohalide as it enters the bed. A Vycor® reservoir, vented with nitrogen, is attached to the reactor near its base just above the frit to permit the intermittent addition of catalyst, promoter, tin, and/or additional silicon or activated silicon to the reactor. The junction of the reservoir and the reactor is normally kept closed by a valve. A single thermocouple is placed vertically through the top of the reactor into the bed of silicon or activated silicon particles. The thermocouple provides the feedback and readout temperature signal to the heater/controller device. Electrical heating wire and fiberglass insulation are wrapped along the entire length of the reactor. The two ends of the heating wire are connected to the heater/controller device. At its top, the reactor connects to the condensing chamber by a Vycor® side arm 2.5 cm internal diameter and 20 cm long. The condensing chamber is maintained at $-63°$ C. to $-78°$ C. with solid carbon dioxide and isopropanol. Condensed samples of the reaction product are withdrawn, usually hourly, into weighed containers. Unreacted organohalide is allowed to distill off at 23° C.–30° C. and the residue analyzed by gas chromatography and gas chromatography-/mass-spectrometry. Reactor A is used only at atmospheric pressure.

Reactor B is a stainless steel fluidized-bed reactor 183 cm long × 5.08 cm internal diameter. A sintered metal frit at its base supports the silicon or activated silicon bed and disperses the gaseous organohalide as it enters the bed. A flanged stainless steel reservoir, vented with nitrogen, is attached to the reactor near its base just above the frit to permit the intermittent addition of catalyst, promoter, tin, and/or additional silicon or activated silicon to the reactor. The junction of the reservoir and the reactor is normally kept closed by a valve. Two thermocouples are located in the bed of silicon or activated silicon. One provides feedback to the heater/controller device; the other is attached to a digital thermometer. Electrical heaters covered with insulation on the outer surface are placed along the full length of the reactor. The heaters are connected to the heater/controller device. There is a gauge at the top of the reactor to measure the pressure. The outlet of the reactor is connected to a stainless steel cyclone which is attached to sintered metal filter. Separation of elutriated solid from the gaseous reactor effluent is accomplished in the cyclone and filter. A refrigerated, $-10°$ C. to $-78°$ C., condensing chamber is connected to the outlet of the filter. A back-pressure control valve located downstream of the condenser outlet permits operation of Reactor B at pressures up to 60 psig. Sampling and analysis are performed as described above for Reactor A.

For both reactors the gaseous organohalide is conveyed from its commercial cylinder to the reactor through stainless steel tubing. The gas is passed through a packed bed of Drierite® prior to entry into the reactor in order to remove traces of moisture. Of course, all flowmeters are calibrated volumetrically with the appropriate gas by a wet-test meter and/or gravimetrically by condensing and weighing metered quantities of liquified gas. All gas flow rates mentioned in the Examples are referred to 1 atm and 21° C.

The Copper Catalysts Used

Tables 2 and 3 present a summary of the properties of the commercial copper catalysts used to illustrate the process of this invention. Both cement and non-cement catalysts are represented in the Tables. Table 2 presents the percentages of total copper, metallic copper, cuprous oxide, cupric oxide, chloride, sulphate, and water in the catalysts. Also shown are the BET surface areas and the average particle size (dp) of the catalysts. Table 3 gives the concentrations of the elements, Al, Fe, Pb, As, Sb, Sn, Mg, Zn, and Cd, all in parts per million (that is, micrograms of element per gram of catalyst). The catalysts used cover a range of BET surface areas, viz, 1–8.0 m$^2$/gm and average particle sizes (dp) viz, 1.7–5.4 microns, which are considered representative of commercial catalysts.

Tables 2 and 3 are set forth below:

TABLE 2

Properties of Copper Catalysts Used to Illustrate the Instant Invention

| Copper Catalyst | Total Cu | Cu° | Cu$_2$ | CuO | Cl$^-$ | SO$_4^{2-}$ | H$_2$O | Area | dp |
|---|---|---|---|---|---|---|---|---|---|
| C1 | 87.1 | 17.6 | 36.5 | 46.4 | 0.015 | 0.02 | 0.082 | 1.06 | 2.3 |
| C2 | 83.7 | 23.5 | 46.9 | 23.2 | — | — | — | 3.2 | 3.9 |
| C3 | 83.8 | 21.2 | 46.5 | 26.5 | — | — | — | 3.2 | 3.9 |
| C4 | 87.2 | 12.2 | 51.5 | 36.5 | 0.029 | 0.004 | 0.092 | 2.02 | 2.05 |
| C5 | 87.9 | 14.6 | 44.4 | 42.3 | 0.009 | 0.011 | 0.01 | 1.59 | 2.2 |
| C6 | 85.4 | 12.5 | 51.1 | 34.4 | 0.005 | 0.006 | 0.1 | 1.56 | 2.4 |
| C7 | 81.52 | 1.66 | 10.13 | 88.58 | 0.015 | 0.017 | 0.04 | 1.12 | 2.2 |
| C8 | 88.1 | 31.0 | 15.8 | 53.9 | — | — | 0.02 | 1.56 | — |

TABLE 2-continued

Properties of Copper Catalysts Used to Illustrate the Instant Invention

| Copper Catalyst | Total Cu | Cu° | Cu₂ | CuO | Cl⁻ | SO₄²⁻ | H₂O | Area | dp |
|---|---|---|---|---|---|---|---|---|---|
| C9  | 87.7  | 11.1  | 64.7  | 24.0  | —     | —     | 0.02  | 3.26 | 5.40 |
| C10 | 87.1  | 20.0  | 33.3  | 46.9  | 0.015 | 0.015 | 0.01  | 1.0  | 2.5  |
| C11 | 87.1  | 19.2  | 31.5  | 49.9  | 0.015 | 0.014 | 0.032 | 1.18 | 2.4  |
| C12 | 87.2  | 18.3  | 32.6  | 49.9  | 0.015 | 0.01  | 0.083 | 2.95 | 1.7  |
| C13 | 81.8  | 22.0  | 50.4  | 18.8  | 0.02  | 1.76  | 0.02  | 8.00 | 4.7  |
| C14 | 80.4  | 11.3  | 34.7  | 47.9  | 0.01  | 0.21  | 0.09  | 1.11 | 2.35 |
| C15 | 85.0  | 16.0  | 28.4  | 54.8  | 0.019 | 0.073 | 0.09  | 1.05 | 3.65 |
| C16 | 87.46 | 13.04 | 74.42 | 12.69 | —     | —     | 0.06  | 2.17 | 3.97 |
| C17 | 83.4  | 14.4  | 30.9  | 51.9  | 0.02  | 0.26  | 0.23  | 1.82 | 2.21 |
| C18 | 86.18 | 8.4   | 62.03 | 28.4  | —     | —     | —     | 2.8  | —    |

Area in m²/gm, dp in microns. All other values in weight percent.

TABLE 3

Trace Metal Content (ppm) of the Copper Catalysts Used to Illustrate the Instant Invention

| Copper Catalyst | Al | As | Cd | Fe | Mg | Pb | Sb | Sn | Zn |
|---|---|---|---|---|---|---|---|---|---|
| C1  | <49   | <57   | <19.7 | 86    | <9.8 | <49  | <49   | 48   | <29   |
| C2  | 88.6  | <24.6 | <9.8  | 160   | <4.9 | <47  | <24.6 | 85.5 | 47.5  |
| C3  | <23.9 | <23.9 | <10   | 126   | <4.8 | <47  | <23.9 | 91.3 | 44.3  |
| C4  | 217   | <29.5 | <9.3  | 96.6  | <4.6 | 116  | <23.3 | 96.2 | 143   |
| C5  | <24   | <24   | <9.6  | 190   | 9.1  | 113  | <23   | 126  | 42.4  |
| C6  | <23.8 | <23.8 | <9.5  | 118   | <4.7 | <48  | <23.8 | 103  | 57.4  |
| C7  | <23   | <22.6 | <9    | 88.1  | <4.5 | <40  | <22.6 | 244  | 17    |
| C8  | 418   | <23.9 | <9.55 | 196   | 5.1  | 87.5 | <23.9 | 806  | 57    |
| C9  | <24.2 | <24.2 | <9.7  | 227   | 6.7  | 134  | <24.2 | 1060 | 70.3  |
| C10 | 45.7  | 65.4  | 33.3  | 130   | <9   | 86.0 | 127   | 1100 | <27.5 |
| C11 | <23   | <23   | <9.3  | 85.9  | <4.5 | <43  | <23   | 1160 | <14   |
| C12 | <24.3 | <24.3 | <9.7  | 716   | <4.8 | <43  | <24.3 | 1150 | <14.6 |
| C13 | 2070  | 892   | <10   | 16400 | 468  | 358  | <24.9 | 1200 | 987   |
| C14 | 3820  | <9    | 183   | 8020  | 4190 | 109  | <22.8 | 1780 | 214   |
| C15 | 100   | <10   | <10   | 800   | 100  | 300  | <22   | 101  | <29   |
| C16 | <23   | <23   | 23    | 94.8  | 9.1  | <49  | <23   | 847  | <13   |
| C17 | 1050  | 83.5  | 142   | 5970  | 654  | 140  | <24   | 1590 | 416   |
| C18 | <24   | <24   | <9    | 122   | <5   | <55  | <39   | 2600 | 219   |

Abbreviations Used

Abbreviations used in the presentation of the experimental data are the following: MD=MeHSiCl₂, DM=Me₂SiHCl, M=Me₃SiCl, T=MeSiCl₃, D=Me₂SiCl₂, HVS=higher boiling (>70° C.) fraction. Where the sum of the percentages of MD, M, T, D, and HVS is less than one hundred percent, the balance (usually less than 0.3 wt %) is believed to be HSiCl₃ and Me₂SiHCl. The quantity of each methylchlorosilane is shown in the Tables as percent by weight. Selectivity, D/T, is shown as a dimensionless gravimetric ratio. Rate is given in weight percent silicon conversion per hour.

EXAMPLES 1A–1Q

These Examples illustrate the effect of tin content on the rate and selectivity in the Direct Reaction, as well as the effect of varying the promoter/tin ratio.

Each of Examples 1A through 1Q was performed in Reactor A using one of the copper catalysts listed in Tables 2 and 3. In each experiment, 210 gm of 65×150 mesh (that is 104–208 microns) technical grade silicon (98.4% Si, 0.35% Al, 0.55% Fe) and 5.0 gm copper catalyst were mixed and heated together to 325° C. in Reactor A, using dry nitrogen as the fluidizing gas.

The nitrogen flow rate was 750 ml/min, measured at 1 atm and 21° C. Thereafter, nitrogen flow was discontinued and HCl at 0.9 lit/min (measured at 1 atm and 21° C.) was admitted to the reactor for 75 minutes. During that time, 8–10 percent of the silicon charged was converted to chlorosilanes, principally trichloro-silane, which were condensed in the refrigerated chamber. Upon termination of HCl flow, nitrogen was again admitted to the bed for 15 minutes to desorb residual chlorosilanes from the activated silicon particles.

0.5 gm anhydrous ZnCO₃ was then charged to the activated silicon particles while under nitrogen fluidization at 325° C. The ZnCO₃ was placed in the above-mentioned reservoir attached to the base of the reactor and injected into the latter with a pulse of dry nitrogen. Thereafter, additional ZnCO₃ (0.2 gm) was injected hourly in the same manner. Methyl chloride at 750 ml/min (measured at 1 atm and 21° C.) was substituted for nitrogen as the fluidizing gas and the reaction continued at 325° C. for a minimum of 4 hours.

Gas chromatographic analysis of the hourly samples showed that steady-state conditions in the bed were attained in 2–6 hours. The steady-state composition in weight percent and performance parameters for the reactions performed with each of the copper catalysts are shown in Table 4. Also shown in Table 4 is the initial tin concentration in the activated silicon calculated on the basis of the silicon charged to the reactor and the tin content of the respective catalysts (see Table 3). The values are reported in parts per million (viz. —micrograms per gram). The ratio, Zn/Sn, is the zinc to tin ratio at the outset of the Direct Reaction. The zinc content of the activated silicon was calculated from the weight of ZnCO₃, the percentage (52.14 wt %) of Zn in ZnCO$_3$, and the zinc concentration of the copper catalyst.

Table 4 is set forth below:

TABLE 4

Effect of Tin Content of Activated Silicon On Rate and Selectivity

| Example | Catalyst | MD | M | T | D | HVS | Sn | Zn/Sn | D/T | Rate |
|---|---|---|---|---|---|---|---|---|---|---|
| 1A | C1 | 8.39 | 1.72 | 8.96 | 79.94 | 0.99 | 1.10 | 1245 | 8.92 | 0.35 |
| 1B | C2 | 3.49 | 1.46 | 6.87 | 85.70 | 2.48 | 2.00 | 685 | 12.48 | 1.10 |
| 1C | C3 | 3.70 | 1.42 | 7.73 | 85.40 | 1.74 | 2.20 | 623 | 11.04 | 0.85 |
| 1D | C4 | 2.80 | 1.68 | 7.29 | 85.99 | 2.24 | 2.30 | 596 | 11.80 | 1.13 |
| 1E | C5 | 1.95 | 1.62 | 5.84 | 86.70 | 3.89 | 3.00 | 457 | 14.85 | 1.27 |
| 1F | C6 | 1.89 | 1.89 | 4.79 | 89.87 | 1.56 | 2.50 | 548 | 18.77 | 0.90 |
| 1G | C7 | 2.01 | 1.41 | 4.42 | 89.76 | 2.41 | 5.80 | 236 | 20.32 | 1.8 |
| 1H | C8 | 0.80 | 2.05 | 4.44 | 87.81 | 4.90 | 19.20 | 71 | 19.77 | 3.36 |
| 1J | C9 | 0.80 | 2.17 | 4.68 | 90.08 | 2.28 | 25.20 | 54 | 19.27 | 4.05 |
| 1K | C10 | 0.80 | 1.60 | 4.01 | 88.97 | 4.61 | 26.20 | 52 | 22.17 | 2.8 |
| 1L | C11 | 0.80 | 1.70 | 4.40 | 87.79 | 5.31 | 27.60 | 50 | 19.93 | 2.7 |
| 1M | C12 | 0.70 | 1.60 | 3.81 | 85.97 | 7.92 | 27.40 | 50 | 22.58 | 3.5 |
| 1N | C13 | 0.70 | 1.90 | 3.41 | 88.98 | 5.01 | 28.60 | 49 | 26.12 | 3.21 |
| 1P | C14 | 0.70 | 1.90 | 4.00 | 88.81 | 4.60 | 42.40 | 32 | 22.22 | 3.40 |
| 1Q | C18 | 0.60 | 2.38 | 3.93 | 88.32 | 4.77 | 63.10 | 20 | 22.47 | 3.70 |

Table 4 shows that the reaction rate and D/T at steady-state increase as the initial tin concentration of the activated silicon is increased up to about 10 ppm Sn (that is 0.001 wt %) and remain relatively constant as the initial tin concentration of the activated silicon is further increased. The linear correlation between rate or D/T and the logarithm of the initial tin concentration is a general one.

These Examples also show that consistent D/T and rate are obtained at Zn/Sn ratios between 20-250. MeHSiCl$_2$ (MD) decreases with increasing tin concentration, as well as with decreasing Zn/Sn. Generally, the higher boiling fraction, HVS (also termed "heavies") increases in content as the tin concentration of the activated silicon increases or as the Zn/Sn ration decreases. The HVS content is generally less than 8 wt % and more usually lies in the 2-5 wt % range.

EXAMPLES 2A-2E

These Examples show the effect on the rate and selectivity in the Direct Reaction upon addition of tin as SnO.

Reactor A was used in these Examples. The copper catalyst, C1, whose low selectivity (D/T) and rate are evident from Table 4, was spiked with 0.05 wt % to 0.25 wt % of SnO; and the mixture blended with the 210 gm of 65×150 mesh technical grade silicon. Activation and Direct Reaction then were done at 325° C. as described in Examples 1A-1Q. The steady-state sample compositions and performance parameters are summarized in Table 5:

As can be seen, both rate and selectivity (D/T) are improved substantially by the addition of tin as SnO. D/T values of about 20 and rates greater than 2 wt % Si conversion per hour are obtained for Sn concentrations greater than 20 ppm and initial Zn/Sn ratios of about 20-60. The decrease in MeHSiCl$_2$ (MD), and the increase in higher boilers (HVS) as Sn concentration increases, which was observed in Examples 1A-1Q, also is observed in these Examples.

These Examples illustrate that the intentional addition of divalent tin (e.g. SnO) to a copper catalyst of poor performance, such that the tin concentration of the catalyst lies between 0.04% -0.22% by weight, results in the formation of an improved copper catalyst for the Direct Reaction.

EXAMPLES 3A-3D

These Examples further illustrate the effects of intentional addition of tin to copper catalysts considered to provide less than satisfactory performance.

In these Examples, reaction parameters for two poorly performing copper catalysts were improved by the addition of SnO to the silicon prior to activation. Two pairs of experimental data are shown in Table 6 below. Each pair is a comparison of the product composition and performance parameters for two Direct Reaction experiments, one with the as received poorly-performing catalyst and the other with 0.15 wt % SnO (based on the weight of copper catalyst) added to the silicon prior to blending with the copper catalyst. Activation with HCl and reaction with methyl chloride at 325° C. were carried out as described in Examples 1A-1Q.

Table 6 is set forth below:

TABLE 5

Improvement in the Performance of Copper Catalyst C1 By Additions of SnO

| Example | % SnO in C1 | MD | M | T | D | HVS | Sn | Zn/Sn | D/T | Rate |
|---|---|---|---|---|---|---|---|---|---|---|
| 2A | 0 | 8.39 | 1.72 | 8.96 | 79.94 | 0.99 | 1.1 | 1245 | 8.92 | 0.35 |
| 2B | 0.05 | 1.33 | 1.13 | 3.93 | 91.79 | 1.82 | 11.6 | 118 | 23.35 | 1.30 |
| 2C | 0.10 | 0.96 | 1.38 | 3.95 | 91.05 | 2.66 | 22.1 | 68 | 23.04 | 2.40 |
| 2D | 0.15 | 0.90 | 1.76 | 3.84 | 88.99 | 4.51 | 32.6 | 42 | 23.20 | 3.60 |
| 2E | 0.25 | 0.68 | 1.59 | 3.62 | 88.67 | 5.43 | 60.7 | 22 | 24.49 | 3.00 |

TABLE 6

Reproducible Rate and (D/T) Improvements Caused by SnO Addition to Silicon

| Example | Catalyst | % SnO | MD | M | T | D | HVS | Sn | Zn/Sn | D/T | Rate |
|---|---|---|---|---|---|---|---|---|---|---|---|
| 3A | C15 | 0 | 4.51 | 1.79 | 6.91 | 84.27 | 2.52 | 2 | 521 | 12.20 | 0.71 |
| 3B | C15 | 0.15 | 1.56 | 1.70 | 4.79 | 86.30 | 5.64 | 34 | 37 | 18.02 | 1.9 |
| 3C | C3 | 0 | 2.98 | 1.40 | 6.83 | 86.99 | 1.80 | 2 | 521 | 12.74 | 0.85 |
| 3D | C3 | 0.15 | 0.61 | 1.72 | 4.27 | 88.35 | 5.92 | 34 | 37 | 20.69 | 2.0 |

As can be seen, within the limits of experimental error, the rates and selectivities are the same for the activated silicon prepared with as-received catalysts, C3 and Cl5. Addition of the same amount of SnO to the silicon used to prepare the activated silicon results in comparable performance parameters. Thus, these Examples demonstrate the reproducible rate and D/T improvements which arise from the presence of tin, in appropriate amounts, in the activated silicon.

EXAMPLES 4A–4L

These Examples show the effect on the performance obtained when using excessive tin concentrations or inadequate promoter/Sn ratios, and, as well, illustrate the performance obtained when the promoter/Sn ratio is maintained in the desired range throughout the course of the Direct Reaction. The effects of using an extremely low level of copper catalyst are also set forth.

In each Example, Reactor B was charged with 830 gm, 65×150 mesh technical grade silicon and either copper catalyst Cl4 or Cl7 at the loadings indicated in Table 7. Tin, either as SnCl2 (Examples 4A through 4D) or Sn metal (Examples 4G and 4J) was added to the mixture of catalyst and silicon to arrive at the concentrations shown in Table 7. The tin impurity levels in the copper catalysts, Cl4 and Cl7 (See Table 3), were taken into account in the calculation of the total tin concentration of the solids to be activated.

Activation with HCl and reaction with methyl chloride were performed at 325° C. and atmospheric pressure as described for Reactor A in the Example 1 series, except that the nitrogen flow was 1.5 lit/min, the HCl flow was 1.3 lit/min and the methyl chloride flow was 2.0 lit/min, all measured at 1 atm and 21° C. In addition, the initial and hourly additions of ZnCO3 were varied so as to provide a range of Zn/Sn ratios lower than that shown in the Example 1 series. Hourly additions of tin (as SnCl2) also were made in some experiments (Examples 4A through 4D).

The hourly ZnCO3 and tin aliquots were mixed with quantities (see Table 7) of mass, i.e., silicon and copper catalyst, having the same copper catalyst loading as the initial mixture for activation and charged to the reactor through the previously described reservoir with a pulse of dry nitrogen. All reactions were 7–8 hours duration; steady-state usually was attained after 2–7 hours.

Table 7 setting forth the conditions employed, and Table 8, showing the steady-state compositions and the performance obtained are set forth below:

TABLE 7

Conditions Used in the Experiments

| Example | Catalyst | Catalyst Loading | Tin Source | Initial Tin | Hourly Tin | Initial ZnCO3 | Hourly ZnCO3 | Hourly Mass | Duration |
|---|---|---|---|---|---|---|---|---|---|
| 4A | C14 | 5.26% | SnCl2 | 620 ppm | 6.87 mg | 0.83 gm | 0.25 gm | 17.14 gm | 7 hr |
| 4B | C17 | 5.11 | SnCl2 | 618.5 | 3.79 | 1.7 | 0.5 | 14.38 | 8 hr |
| 4C | C17 | 2.57 | SnCl2 | 722 | 3.60 | 2.4 | 1.0 | 11.63 | 8 hr |
| 4D | C14 | 5.26 | SnCl2 | 557 | 5.09 | 1.7 | 0.5 | 26.29 | 7 hr |
| 4E | C14 | 5.26 | — | 99.6 | 1.66 | 1.8 | 0.5 | 16.63 | 8 hr |
| 4F | C17 | 2.56 | — | 40.8 | 0.64 | 0.85 | 0.25 | 15.57 | 7 hr |
| 4G | C17 | 1.25 | Sn° | 43.0 | 0.32 | 1.7 | 0.5 | 16.13 | 8 hr |
| 4H | C17 | 2.57 | — | 40.8 | 0.71 | 1.7 | 0.5 | 17.38 | 8 hr |
| 4J | C17 | 0.81 | Sn° | 78.6 | 0.31 | 3.7 | 0.75 | 17.88 | 8 hr |
| 4K | C17 | 2.56 | — | 40.8 | 0.56 | 3.4 | 1.0 | 13.88 | 8 hr |
| 4L | C17 | 0.81 | — | 12.82 | 0.26 | 1.7 | 0.5 | 15.13 | 8 hr |

TABLE 8

Steady-State Compositions and Performance Parameters for the Experiments of Example 4

| Example | MD | M | T | D | EVS | Sn | Initial Zn/Sn | D/T | Rate | Hourly Zn/Sn |
|---|---|---|---|---|---|---|---|---|---|---|
| 4A | 1.23 | 2.77 | 27.91 | 60.29 | 8.19 | 620 ppm | 0.81 | 2.16 | 0.55 | 19 |
| 4B | 0.49 | 5.76 | 23.58 | 66.73 | 3.93 | 618.5 | 1.70 | 2.83 | 0.70 | 69 |
| 4C | 0.58 | 4.97 | 12.78 | 76.32 | 4.67 | 722 | 2.83 | 5.97 | 1.15 | 145. |
| 4D | 0.46 | 4.49 | 12.54 | 77.73 | 4.04 | 557 | 2.91 | 6.2 | 1.32 | 51. |
| 4E | 0.94 | 2.28 | 4.93 | 88.12 | 3.37 | 99.6 | 10.99 | 17.88 | 2.36 | 157. |
| 4F | 0.72 | 2.06 | 5.29 | 90.07 | 1.65 | 40.8 | 12.69 | 17.04 | 1.53 | 204. |
| 4G | 0.41 | 1.68 | 3.91 | 91.63 | 2.30 | 43.0 | 24.41 | 23.43 | 1.75 | 815. |
| 4H | 0.34 | 2.00 | 3.13 | 90.61 | 3.89 | 40.8 | 26.25 | 28.9 | 2.32 | 367. |
| 4J | 0.61 | 2.11 | 4.86 | 87.80 | 4.64 | 78.6 | 29.18 | 18.06 | 1.37 | 1262. |
| 4K | 0.57 | 1.77 | 5.08 | 90.24 | 2.29 | 40.8 | 51.47 | 17.78 | 1.30 | 931. |
| 4L | 1.00 | 1.90 | 6.36 | 89.13 | 1.52 | 12.82 | 83.55 | 14.02 | 0.41 | 1003. |

These Examples, as can be seen from Table 8, show that, for activated silicon, Zn/Sn ratios less than about 10 and Sn concentrations greater than about 100 ppm are disadvantageous to both reaction rate and D/T. For reactor B, from the data obtained, the optimum Sn concentration is about 40–100 ppm and Zn/Sn about 24-40. Hence, these Examples show that the exact value of the Zn/Sn ratio corresponding to optimum steady-state rate and D/T can change from one reactor to another.(compare the Example 1 series), but that this value still falls within the broad range 10-250.

These Examples also demonstrate (compare Examples 4JF, 4G and 4H) that the steady-state rate and D/T depend not only on the initial Sn concentration of the activated silicon, but also on maintaining the Zn/Sn ratio within the desired range during the reaction (that is, both the initial Zn/Sn ratio as well as that of the activated silicon subsequently supplied to the reactor).

A comparison of Examples 4E, 4G, 4J and 4L shows that the copper catalyst loading may be reduced from approximately 5 wt % to 2.5 wt % and even to 0.8 wt %; and the Direct Reaction can still yield steady-state rates greater than 1 wt % Si conversion per hour and a steady-state D/T greater than about 18, provided the Sn concentration of the activated silicon and the Zn/Sn ratio are maintained within their optimum ranges of 10-100 ppm and 10-100, respectively. Clearly, the poor performance in Example 4L arose from the low overall Sn concentration brought about by the high Zn/Sn ratio of the added mass. Examples 4G and 4J also demonstrate the effectiveness of zerovalent tin in improving the performance of an activated silicon in the Direct Reaction.

EXAMPLE 5

This Example shows the improvement in performance obtained from a catalyst (Example 1E), considered to have provided mediocre performance, by providing increased tin levels and a more desirable promoter/Sn ratio, even at a reduced catalyst level. The results also illustrate the ability to predict selectivity (D/T), based upon the initial tin level and the promoter/Sn ratio.

Using Reactor B, the mixture for activation comprised a blend of 841.5 gm, 65×150 mesh technical grade silicon, 8.50 gm copper catalyst $C_5$, and 0.064 gm $CuSnO_3$ The Sn concentration was 40.5 ppm, taking into account both the tin introduced by $CuSnO_3$ and that introduced by the copper catalyst $C_5$.

Activation with HCl and Direct Reaction with methyl chloride at 325° C. were performed as described in the Example 4 series. Following the activation with HCl, 1.8 gm $ZnCO_3$, plus 30 gm of the silicon and copper catalyst mixture containing 1.01 wt % $C_5$, were added to the reactor through the reservoir.

Thereafter, hourly additions averaging 14.14 gm of the silicon and copper catalyst mixture and 0.5 gm $ZnCO_3$ were made. The initial Zn/Sn ratio was 27.59 and that of the hourly additions was 14324. $CuSnO_3$ aliquots were not added during the reaction. The experimental data are summarized in Table 9:

TABLE 9

Direct Reaction Steady-State Composition and Performance Parameters For Silicon Activated with $CuSnO_3$ and Copper Catalyst $C_5$

| MD | M | T | D | HVS | Sn | Initial Zn/Sn | D/T | Rate |
|---|---|---|---|---|---|---|---|---|
| 0.64 | 1.74 | 3.78 | 91.65 | 2.29 | 40.5 ppm | 27.59 | 24.22 | 1.36 |

In Table 8, it was shown that both an initial tin concentration of 40-43 ppm and initial Zn/Sn of 24-30 were accompanied by a D/T of 23-29. In this Example, the initial Sn was 40.5 ppm and initial Zn/Sn was 27.59. Accordingly, the steady-state value of D/T =24.22 falls within the range predicted by the results of the Example 4 series.

Additionally, the results affirm the effectiveness of $CuSnO_3$, a tetravalent tin compound, in improving the performance of an activated silicon in the Direct Reaction.

The results herein can be contrasted with the results in Example 1E wherein use of copper catalyst $C_5$ provided a D/T of only 14.85 at a loading of 2.5 wt % of the silicon charged to the reactor.

EXAMPLE 6

This Example shows the effects of the addition of tin or a tin compound on the performance of the reaction while the Direct Reaction is already in progress.

Reactor B was used for the activation with HCl and reaction with methyl chloride as described in the Example 4 series. 6.8 gm copper catalyst $Cl_7$ and 843.2 gm 65×150 mesh technical grade silicon (i.e. 0.81% copper catalyst $Cl_7$ based on the silicon used) were blended together and activated with HCl as previously described. Following activation, 1.7 gm $ZnCO_3$, plus 30 gm of the 0.81% copper catalyst ($Cl_7$) and silicon mixture, were charged to the reactor through the reservoir. Thereafter, hourly additions averaging 10.14 gm/hr of the 0.81% copper catalyst ($Cl_7$) and silicon mixture and 0.5 gm $ZnCO_3$ were made to the reactor. The initial Sn concentration based on the silicon used was 12.82 ppm.

At the end of eight hours, 26.0 mg metallic tin mixed with 30.0 gm of the 0.81% copper catalyst ($Cl_7$) and silicon mixture and 1.8 gm $ZnCO_3$ were charged to the reactor through the reservoir and the reaction continued for an additional eight hours. Hourly mass (i.e., 0.81% catalyst $Cl_7$ plus silicon) additions averaging 16.29 gm and 0.5 gm $ZnCO_3$ were made during this time. The maximum tin concentration at the beginning of the second period was calculated to be 43.0 ppm (based on silicon in the reactor at the beginning of the ninth hour) assuming no losses due to elutriation.

Table 10 sets forth the composition and performance data:

TABLE 10

Beneficial Effect of Tin Addition (9-16 hr) To a Poorly Performing Activated Silicon

| Time, hr | MD | M | T | D | HVS | D/T | Rate |
|---|---|---|---|---|---|---|---|
| 1 | 5.85 | 12.82 | 11.58 | 34.86 | 0.88 | 3.0 | 0.31 |
| 2 | 2.35 | 2.48 | 8.89 | 83.77 | 1.59 | 9.0 | 0.46 |
| 3 | 1.38 | 2.17 | 7.25 | 86.82 | 2.04 | 12.0 | 0.28 |
| 4 | 1.63 | 2.04 | 6.27 | 88.40 | 1.57 | 14.1 | 0.43 |
| 5 | — | 1.35 | 6.39 | 90.51 | 1.75 | 14.2 | 0.47 |
| 6 | 1.15 | 2.06 | 6.13 | 88.85 | 1.59 | 14.5 | 0.37 |
| 7 | 1.26 | 1.94 | 6.37 | 89.10 | 1.36 | 14.0 | 0.39 |
| 8 | 1.16 | 2.09 | 6.66 | 88.75 | 1.33 | 13.3 | 0.41 |
| 9 | 2.49 | 1.55 | 5.33 | 81.49 | 1.40 | 15.3 | 1.76 |
| 10 | 0.50 | 1.71 | 4.03 | 91.38 | 2.40 | 22.7 | 1.81 |
| 11 | — | 1.65 | 3.63 | 92.02 | 2.69 | 25.4 | 1.79 |
| 12 | 0.38 | 1.65 | 4.09 | 91.91 | 1.93 | 22.5 | 1.71 |
| 13 | 0.48 | 1.71 | 3.77 | 91.77 | 2.20 | 24.3 | 1.80 |
| 14 | 0.40 | 1.78 | 3.93 | 91.06 | 2.48 | 23.2 | 1.76 |
| 15 | 0.62 | 1.86 | 4.12 | 91.02 | 2.37 | 22.1 | 1.71 |
| 16 | 0.56 | 1.42 | 3.86 | 92.02 | 2.12 | 23.8 | 1.64 |

As can be seen from Table 10, the positive effect of the tin addition is observed within two hours. D/T increased from 13.3 to 22.7 from the eighth to the tenth hour, and rate increased from 0.41% Si conversion per hour to 1.81% Si conversion per hour in the same period. The improvements were sustained for the next six hours of the experiment. Thus, by comparing the first eight hour period, and the second eight hour period it is shown that the addition of tin to improve the performance of an activated silicon may be made while the Direct Reaction is already in progress.

EXAMPLE 7

This Example shows that the mixture of copper catalyst and silicon can be activated with hydrogen.

Reactor A was used with a blend of 210 gm, 65×150 mesh technical grade silicon and 5.0 gm copper catalyst C10. The mixture of solids was heated to 400° C. while being fluidized in dry nitrogen at 750 ml/min (measured at 1 atm and 21° C.). Hydrogen at 1 lit/min was then introduced, and the temperature maintained at 400° C. for 2 hours. Thereafter, nitrogen was re-introduced; and the reactor cooled to 325° C. An initial charge of 0.5 gm $ZnCO_3$ was made to the reactor through the reservoir. Subsequently, hourly additions of 0.2 gm $ZnCO_3$ were made. Nitrogen flow was discontinued, and methyl chloride at 750 ml/min was added to the bed of activated silicon particles. The reaction was continued for 10 hours.

The composition and performance data are set forth in Table 11:

TABLE 11

Hourly Composition and Performance Parameters For The Direct Reaction With Silicon Acitivated with Copper Catalyst C10 and Hydrogen

| Time hr | DM | MD | M | T | D | HVS | D/T | Rate |
|---|---|---|---|---|---|---|---|---|
| 1 | 0.23 | 0.11 | 3.51 | 25.67 | 65.46 | 4.87 | 2.55 | 0.18 |
| 2 | 0.11 | 1.34 | 3.13 | 18.19 | 71.19 | 5.98 | 3.91 | 0.96 |
| 3 | 0.11 | 1.26 | 2.40 | 9.03 | 80.67 | 6.52 | 8.94 | 1.12 |
| 4 | 0.11 | 1.61 | 2.07 | 6.23 | 84.08 | 5.89 | 13.50 | 1.59 |
| 5 | 0.06 | 0.67 | 1.57 | 5.86 | 88.50 | 3.36 | 15.10 | 1.86 |
| 6 | 0.05 | 0.81 | 1.62 | 4.86 | 87.85 | 4.86 | 18.08 | 1.88 |
| 7 | 0.05 | 0.68 | 1.94 | 5.26 | 87.86 | 4.23 | 16.70 | 2.04 |
| 8 | 0.07 | 0.80 | 1.60 | 4.68 | 88.01 | 4.80 | 18.81 | 1.91 |
| 9 | 0.07 | 0.68 | 1.71 | 4.54 | 88.00 | 5.00 | 19.38 | 1.92 |
| 10 | 0.06 | 0.68 | 1.82 | 4.88 | 88.26 | 4.31 | 18.09 | 1.84 |

Table 11 shows that steady-state was attained at about 6 hours and that the steady-state D/T and rate were 18.31 and 1.91% Si conversion per hour, respectively.

EXAMPLE 8

This Example shows that commercial cupric hydroxide, $Cu(OH)_2$, is a poor catalyst for the Direct Reaction.

210 gm, 65×150 mesh technical grade silicon and 5.0 gm $Cu(OH)_2$ (surface area 37 m²/gm, purchased from Alfa Products, Danvers, Mass. 01923) were blended together and heated to 395° C. with nitrogen as the fluidizing gas in the manner described in Example 7. Activation was performed with 1 lit/min $H_2$ (measured at 21° C. and 1 atm) in place of HCl for 75 min. With $H_2$ activation and $Cu(OH)_2$, no chlorosilanes are formed.

Following the activation the fluidized-bed was cooled at 325° C. with nitrogen flow. Zinc carbonate addition (0.5 gm) and Direct Reaction with methyl chloride were performed as described in Example 7. After five hours reaction with methyl chloride, at 325° C. only 9.9 gm methylchlorosilanes was formed. The D/T selectivity was 4.47 and the rate was 0.21% Si conversion per hour.

EXAMPLE 9

This Example shows the effect on performance of the addition of tin to the $Cu(OH)_2$ catalyst of Example 8.

The activation and reaction of Example 7 were repeated with 210 gm, 65×150 mesh technical grade silicon, 5.0 gm $Cu(OH)_2$ (surface area 37m²/gm from Alfa Products, Danvers, Mass. 01923), and 0.0055 gm SnO.

Table 12 shows the composition and performance data obtained:

TABLE 12

Improved Rate and (D/T) From SnO Addition to $Cu(OH)_2$ Plus Silicon

| Time Hr | DM | MD | M | T | D | HVS | D/T | Rate |
|---|---|---|---|---|---|---|---|---|
| 1 | 0.14 | 2.65 | 5.41 | 13.03 | 74.21 | 2.19 | 5.75 | 1.3 |
| 2 | 0.08 | 1.88 | 2.32 | 6.59 | 83.19 | 5.87 | 12.62 | 1.6 |
| 3 | 0.05 | 0.82 | 2.36 | 6.06 | 83.13 | 7.52 | 13.72 | 2.0 |
| 4 | 0.04 | 0.73 | 2.40 | 5.10 | 84.96 | 6.78 | 16.66 | 2.8 |
| 5 | 0.03 | 0.53 | 2.46 | 4.38 | 87.71 | 4.88 | 20.03 | 1.9 |
| 6 | 0.08 | 0.62 | 2.76 | 4.00 | 87.30 | 5.82 | 21.83 | 2.1 |
| 7 | 0.03 | 0.33 | 1.79 | 3.33 | 89.81 | 4.72 | 26.97 | 2.8 |
| 8 | 0.03 | 0.34 | 1.61 | 3.08 | 90.27 | 4.66 | 29.31 | 3.2 |
| 9 | 0.01 | 0.31 | 2.38 | 4.34 | 89.11 | 3.86 | 20.53 | 3.8 |
| 10 | 0.01 | 0.38 | 2.04 | 4.11 | 91.91 | 1.54 | 22.36 | 3.7 |

As can be seen in Table 12, the steady-state D/T was greater than 20 and the rate greater than 2.0% Si converted per hour. The initial copper content of the activated silicon was 1.36 wt %, the initial tin content was 23 ppm and the initial Zn/Sn ratio was 54.

This performance can be contrasted with the undesirable performance of the $Cu(OH)_2$ catalyst that was obtained in Example 8.

EXAMPLE 10

This Example illustrates performance of the Direct Reaction at a relatively high temperature.

Example 4E, with 5.26 wt % copper catalyst C14 and 830 gm, 65×150 mesh technical grade silicon, was repeated in Reactor B at 340° C. The reaction was run for twelve hours. At the third hour, steady-state was attained and was maintained for the next nine hours. The steady-state D/T and rate were 18.7 and 3.53% Si conversion per hour, respectively. At 325° C. (Example 4E), the corresponding values were 17.88 and 2.63% Si conversion per hour.

EXAMPLE 11

This Example shows the performance obtained when the copper catalyst is eliminated and tin is employed.

210 gm, 65×150 mesh technical grade silicon and 0.999 gm SnO powder were charged to reactor A and heated to 325° C. using nitrogen as the fluidizing gas. Reaction of the silicon with HCl, zinc carbonate (0.5 gm) addition, and fluidization with CH₃Cl were then performed as described in the Example 1 series. Methyl chloride flow to the reactor at 325° C. was maintained for three hours. None of the hourly samples contained any residue following the distillation of methyl chloride. No methylchlorosilanes were formed.

Thus, tin at 0.42 wt % cannot be used as a replacement for copper in preparing the activated silicon used for the Direct Reaction.

EXAMPLE 12

This Example shows the performance obtained, in the absence of a copper catalyst, using tin at a concentration within the range defined for the activated silicon of this invention.

845.0 gm, 65×150 mesh technical grade silicon and 0.03415 gm tin powder were mixed together on a rolling mill and charged to Reactor B. The tin concentration was 0.004 wt %. The mixture was heated to 325° C. with nitrogen as the fluidizing gas, as described in the Example 4 series. Treatment with HCl, addition of zinc carbonate (1.8 gm mixed with 20 gm of the silicon), and introduction of methyl chloride also were performed as described in Example 4. The duration of methyl chloride flow at 325° C. was four hours.

None of the samples collected contained methylchlorosilanes. All four samples evaporated to dryness during the distillation of the methyl chloride. Thus, the presence of tin at a concentration of 0.004 wt % in the activated silicon is an insufficient condition for the obtention of a reactive, highly selective, activated silicon for the Direct Reaction.

EXAMPLE 13

This Example illustrates the performance obtained at a low catalyst loading, and the effect of the order of addition of the promoter, catalyst and tin.

To the unreactive, tin-containing silicon of Example 12 was charged a mixture of 1.7 gm $ZnCO_3$, 0.01841 gm tin powder, 4.2 gm copper catalyst C₂, and 10.0 gm silicon through the reservoir while the reactor was held at 325° C. under methyl chloride fluidization. Allowing for the 24.36 gm silicon reacted with HCl and the 20.0 gm added initially with the zinc carbonate as was done in Example 12, the reactor now contained a maximum of 850.6 gm silicon. The maximum copper catalyst concentration was 0.49 wt %, the tin concentration was maximally 0.0062 wt % and the zinc maximally 0.21 wt %.

Reaction with methyl chloride was continued at 325° C. for an additional 8 hours. Hourly additions of 0.5 gm $ZnCo_3$, 0.0018 gm Sn powder and 20.0 gm silicon were made to the reactor. No additional copper catalyst was added.

The steady-state D/T reached 27.3±2.5 and the rate 2.54±0.08% Si conversion per hour after only two hours. The reaction was continued for 8 hours.

This Example shows that an inferior copper catalyst such as C₂ (Table 4) may be used at as low a level as 0.49 wt % to obtain superior performance in the Direct Reaction, provided that the tin and zinc level are within the ranges defined for the activated silicon of the invention. This also illustrates that the copper catalyst may be added to the reactor following HCl treatment of the silicon and tin mixture with no loss of performance. Combined with the results of Example 5, this shows that the order of addition of zinc promoter, tin activator and copper catalyst to the silicon is not critical.

EXAMPLE 14

This Example sets forth chemical analyses of certain of the prior Examples and compares the performances obtained.

Samples of activated silicon were taken from the reactors by terminating or interrupting the Direct Reaction at steady-state. The solid samples were digested in HF, $HNO_3$ and $HClO_4$ and analyzed by inductively coupled plasma (ICP) spectrometry, as described by W. Zamechek et al., *Trace Metals Analysis in Silicon and Aluminum Metals by Inductively Coupled Plasma*, APPLICATIONS OF INDUCTIVELY COUPLED PLASMAS TO EMISSION SPECTROSCOPY 169-85 (Symposium, R. Barnes ed.) (Franklin Inst. Press, Philadelphia, Pa. 1977). In Example 5, the activated silicon sample was taken after eight hours reaction, in Example 6 after 16 hours, and in Example 13 after eight hours.

In Example 6, the maximum Sn concentration that could have been present in the activated silicon was 43.0 ppm. Elemental analysis showed 17 ppm Sn, indicating that 39.5% of the tin was retained in the fluidized bed during the second eight hour period of the experiment. The zinc concentration was maintained at 900-1230 ppm with hourly additions of $ZnCO_3$. Consequently, the Zn/Sn ratio was maintained at 24-75 during the experiment and good D/T and rate were observed.

Only 27 wt.% (11/40.5×100) of the initial Sn concentration was retained in the bed of Example 5. The lower rate observed is consistent with the conclusions of Examples 1 and 2. The zinc concentration was kept at 760-1100 ppm with hourly $ZnCO_3$ additions. As a result, Zn/Sn ratios of 27-100 were realized during the experiment. D/T was good, but the rate was lower than when Zn/Sn was more narrowly controlled.

Table 13 sets forth the results of the analyses and the performance data:

TABLE 13

Cu, Sn AND Zn CONCENTRATIONS DETERMINED BY CHEMICAL ANALYSIS OF REACTED ACTIVATED SILICON AT STEADY-STATE

| Example | Sn(ppm) | Zn(ppm) | Cu wt. % | Zn/Sn | D/T | Rate |
|---|---|---|---|---|---|---|
| 6 | 17 ± 1 | 935 ± 65 | 0.31 ± 0.1 | 54 ± 6 | 23.42 | 1.81 |
| 5 | 11.5 ± 0.5 | 748 ± 18 | 0.28 ± 0.01 | 65 ± 1 | 24.22 | 1.36 |
| 13 | 33 ± 5 | 761 ± 38 | 0.21 ± 0.01 | 24 ± 5 | 27.3 | 2.54 |

In Example 13, the initial Zn/Sn ratio was 33.87 and the ratio in the hourly additions was 144.8. This allowed control of Zn/Sn between the narrower limits of 19-34 and both superior rate and D/T were observed.

The analyses made demonstrate that the actual Zn/Sn ratios maintained in the reactor at steady-state are within the range 10-100 when optimum rates and selectivities are observed. It also shows that control of Zn/Sn within the narrow limits of 20-50 gives even more beneficial rates and selectivities. This also shows that superior Direct Rection performance is realized with as little as 0.2-0.3 wt.% copper retained in the activated silicon.

EXAMPLE 15

Based upon the data from prior Examples, this shows the effect on the induction period with a variance in the promoter/tin ratio.

Often, rate and D/T do not attain stable values at the same hour. Hence, in determining the length of the induction period, the longer of the two times is used. The data in Table 14 below are drawn from the experiments described in the Example 4 series and Example 13:

TABLE 14

| | | | The Influence Of Zn/Sn on the Induction Period in the Direct Reaction | | | | | | | | | |
|---|---|---|---|---|---|---|---|---|---|---|---|---|
| Example | Initial Sn(ppm) | Initial Zn/Sn | Hourly Zn/Sn | | 1 Hr | 2 Hr | 3 Hr | 4 Hr | 5 Hr | 6 Hr | 7 Hr | 8 Hr | Induction Period, |
| 4H | 40.8 | 26.25 | 367 | Rate | 1.88 | 2.43 | 2.42 | 2.20 | 2.27 | 2.35 | 2.41 | 2.24 | 2 |
| | | | | (D/T) | 2.7 | 24.7 | 27.5 | 28.4 | 25.1 | 31.9 | 28.4 | 32.1 | |
| 4G | 43.0 | 24.41 | 815 | Rate | 1.76 | 1.81 | 1.79 | 1.71 | 1.80 | 1.76 | 1.71 | 1.64 | 2 |
| | | | | (D/T) | 15.3 | 22.7 | 25.4 | 22.5 | 24.3 | 23.2 | 22.1 | 23.8 | |
| 13 | 62.0 | 33.8 | 145 | Rate | 2.35 | 2.42 | 2.55 | 2.54 | 2.51 | 2.59 | 2.53 | 2.51 | 2 |
| | | | | (D/T) | 24 | 24.6 | 29.2 | 31.0 | 29.5 | 25.8 | 26.7 | 27.4 | |
| 4B | 722 | 2.83 | 145 | Rate | 1.44 | 0.72 | 0.83 | 1.02 | 1.61 | 2.27 | 3.21 | 3.46 | 7 |
| | | | | (D/T) | 0.37 | 3.2 | 4.4 | 5.7 | 7.8 | 10.9 | 16.3 | 15.5 | |
| 4E | 99.6 | 10.99 | 157 | Rate | 1.72 | 2.14 | 2.21 | 2.46 | 2.51 | 2.68 | 2.94 | 3.00 | >7 |
| | | | | (D/T) | 1.5 | 9.2 | 15.9 | 17.4 | 15.9 | 18.8 | 18.0 | 21.3 | |
| 4F | 40.8 | 12.69 | 204 | Rate | 1.01 | 1.39 | 1.53 | 1.46 | 1.36 | 1.65 | 1.65 | — | 6 |
| | | | | (D/T) | 4.6 | 10.4 | 14.9 | 14.7 | 14.4 | 20.3 | 20.9 | — | |
| 4K | 40.8 | 51.47 | 931 | Rate | 0.95 | 1.29 | 1.28 | 1.27 | 1.34 | 1.35 | 1.30 | 1.24 | 3 |
| | | | | (D/T) | 2.5 | 12.8 | 16.8 | 18.7 | 17.5 | 16.4 | 17.0 | 20.3 | |
| 4L | 12.82 | 83.55 | 1003 | Rate | 0.31 | 0.46 | 0.28 | 0.43 | 0.47 | 0.37 | 0.39 | 0.41 | 4 |
| | | | | (D/T) | 3.0 | 9.4 | 12.0 | 14.4 | 14.2 | 14.5 | 14.0 | 13.3 | |

When the initial Zn/Sn is in the range 20–50 (Examples 4H, 4G, 13), steady-state is attained at the second hour. As can be seen, D/T is also greater than 18 and the rate greater than 1.5% Si converted per hour at that time. For initial Zn/Sn values less than 20 (Examples 4B, 4E, 4F), the induction period lasts at least 6 hours. The induction period is at least 3 hours for the Direct Reaction with activation silicon having Zn/Sn greater than 50 (Examples 4K, 4L). The data also show that the length of the induction period can be influenced by the hourly Zn/Sn values.

What is claimed is:

1. An activated silicon composition for use in a reaction with an organo halide comprising silicon and, based on the weight of silicon:
   (a) 0.05 to 1.0 weight percent copper
   (b) 0.05 to 0.2 weight percent zinc
   (c) 0.001 to 0.01 weight percent tin wherein the zinc to tin ratio is 10–100.

2. An activated silicon composition as defined in claim 1 wherein the zinc to tin ratio is 20–50.

3. A process of preparing organohalo silanes which comprises reacting an organo halide with silicon in the presence, based on the weight of silicon, of:
   (a) 0.05 to 1.0 weight percent copper
   (b) 0.05 to 0.2 weight percent zinc
   (c) 0.001 to 0.01 weight percent tin wherein the zinc to tin ratio is 10–100.

4. A process as defined in claim 3 wherein the zinc to tin ratio is 20–50.

5. A process as defined in claim 3 wherein the organo halide is methylchloride.

6. A process as defined in claim 3 conducted in a fluidized bed reactor.

7. A cocatalyst system for catalyzing the reaction between silicon and an organo halide comprising, based on the weight of silicon:
   (a) 0.05 to 1.0 weight percent copper
   (b) 0.05 to 0.2 weight percent zinc
   (c) 0.001 to 0.01 weight percent tin wherein the zinc to tin ratio is 10–100.

8. A cocatalyst system as defined in claim 7 wherein the zinc to tin ratio is 20–50.

* * * * *